United States Patent [19]

Bar-Or et al.

[11] Patent Number: 5,330,898
[45] Date of Patent: Jul. 19, 1994

[54] METHOD FOR THE VERY RAPID DETECTION OF POLYAMINES

[75] Inventors: David Bar-Or, Englewood; Clive Solomons, Denver, both of Colo.

[73] Assignee: Diagnostic Markers, Inc., Englewood, Colo.

[21] Appl. No.: 770,519

[22] Filed: Oct. 3, 1991

[30] Foreign Application Priority Data

Feb. 20, 1991 [IL] Israel .......................... 97318

[51] Int. Cl.$^5$ .................. C12Q 1/04; C12Q 1/06; G01N 21/78
[52] U.S. Cl. ........................... 435/29; 435/4; 435/32; 436/63; 436/106; 436/111; 436/164; 436/811; 436/171
[58] Field of Search ............... 439/32, 29, 4; 436/106, 436/111, 164, 63, 811, 171

[56] References Cited

U.S. PATENT DOCUMENTS 4,169,811 10/1979 Yoshikawa et al. .............. 436/138

OTHER PUBLICATIONS

Hasada, et al. Chem. Abstracts vol. 113, 1990 Abstract No. 138556u.
Lehninger "Biochemistry", Worth Publishers, Inc. 1979 New York pp. 716–717.
Marsh et al, Caries Research 1989 23:348–350 "Antibacterial Activity of Some Plaque-Disclosing Agents and Dyes".
Amsel, R. et al., Non specific vaginitis diagnostic criteria and microbial and epidemiological associations. Amer. J. of Med. 74:14, 1983.
Chen, K. C., et al., Biochemical diagnosis of vaginitis: determination of diamines in vaginal fluids. J. Infect. Dis. 145 (1982) pp. 337–345.
Gardner, H. L., et al. Haemophilus vaginalis vaginitis: A newly defined infection previously classified as non-specific vaginitis. Am. J. Obstet. Gynaecol. 69 (1955) pp. 962–976.
Clarke, S. et. al., Bacterial vaginosis: A comprehensive review. Nursing Clinics of North America 23 (4): 865, 1988.
Nelson, M. S., Clinical diagnosis of bacterial vaginosis. Amer. J. of emergency medicine, 5:488, 1987.
Sehgal, S. C., et. al., Role and prevalence of Gardnerella vaginitis in anaerobic vaginosis. Infection 18 No. 2 83/25 to 85/27, 1990.
Livengood, C. H., et. al., Bacterial vaginosis: Treatment with topical intravaginal Clindamycin Phosphate. Obstet. & Gynecol, 76, No. 1, 118–123.
Spiegel, C. A., et. al., Diagnosis of bacterial vaginosis by direct gram stain of vaginal fluids. J. of Clin. Microb., Jul., 1983, pp. 170–177.
Thomason, J. L. et. al., Statistical evaluation of diagnostic criteria for bacterial vaginosis. A. J. Obstet, Gyn. 162, No. 1, 155–160, 1990.
Hillier, S., et al., Microbiologic efficacy of intravaginal Clindamycin cream for the treatment of bacterial vaginosis. Obstet. & Gynecol. 76, No. 3 407–413, 1990.
Eschenbach, D. A., et al., Diagnosis and clinical manifestations of bacterial vaginosis. Am. J. Obstet. & Gynecol., 158, No. 4, 819–828, 1988.

*Primary Examiner*—Michael G. Wityshyn
*Assistant Examiner*—Jane Williams
*Attorney, Agent, or Firm*—Oblon, Spivak, McClelland, Maier & Neustadt

[57] ABSTRACT

A method for the detection of at least one polyamine associated with bacterial infection, which comprises contacting a sample suspected of containing polyamine-associated bacteria in aqueous medium at alkaline pH with indigo carmine and dimethyl sulfoxia and observing whether a blue color develops in five minutes indicating the presence of polyamine.

16 Claims, 1 Drawing Sheet

METHOD FOR THE VERY RAPID DETECTION OF POLYAMINES

FIELD AND BACKGROUND OF THE INVENTION

The present invention relates to a very rapid method for the detection of polyamines, and to a kit for use in such method, in order to diagnose bacterial vaginosis.

In gynecological practice, bacterial vaginosis is one of the major reasons for visits by patients to physicians. Vaginosis associated with Gardnerella, may affect 5–40% of the female population attending medical practices or clinics. Anaerobic infections are accompanied by Gardnerella organisms, which become attached to desquamated vaginal cells. These cells are visible under the microscope as "clue cells". The present diagnosis and treatment of such infections is largely based on clinical symptoms and the microscopic appearance of the vaginal discharge with regard to clue cells. Further characteristics of bacterial vaginosis infections include elevated pH values, a homogenous malodorous vaginal discharge, and the production of a foul odor when potassium hydroxide is added to the discharge (the "whiff" test). Clinical suspicion may be confirmed by elaborate and time consuming microscopic and culturing techniques. Interpretation of the results in the existing methods of diagnosis, and the laboratory techniques involved, require considerable skills. Moreover, Gardnerella cultures do not correspond to the clinical syndrome.

The following is a list of relevant background references.

1. Amsel, R., Totten, P. A., et al, "Non-specific Vaginitis Diagnostic Criteria and Microbial and Epidemiological Associations", Amer. J. Med., 74: 14 (1983).
2. Chen, K. C. S., Amsel, R., Eschenbach, D. A., Holmes, K. K., "Biochemical Diagnosis of Vaginitis: Determination of Diamines in Vaginal Fluids", J. Infect. Dis., 145: 337–345 (1982).
3. Gardner, H. L., Dukes, C. D., "*Haemophilus Vaginalis* Vaginitis: A Newly-Defined Infection previously Classified as Non-Specific Vaginitis", Am. J. Obstet. & Gynaecol., 69: 962–976 (1955).
4. Clarke Secor, R. Mimi, "Bacterial Vaginosis: A Comprehensive Review", Nursing Clinics of North America, 23(4): 865 (1988).
5. Nelson, M. S., "Clinical Diagnosis of Bacterial Vaginosis", Amer. J. of Emergency Medicine, 5: 488 (1987).
6. Sehgal, S. C., Nalini, V., "Role and prevalence of Gardnerella Vaginitis in Anaerobic Vaginosis", Infection, 18(2): 83/25 to 85/27 (1990).
7. Livengood, C. H. III, Thomason, J. L., Hill, G. B., "Bacterial Vaginosis: Treatment with Topical Intravaginal Clindamycin phosphate", Obstet. & Gynaecol., 76(1): 118–123.
8. Spiegel, C. A., Amsel, R., Holmes, K. K., "Diagnosis of Bacterial Vaginosis by Direct Gram Stain of Vaginal Fluid", J. of Clinical Microb., 1983 (July): 170–177.
9. Thomason, J. L., Gelbart, S. M., Anderson, R. J., Walt, A. K., Osypowski, P. J., Broekhuizen, F. F., "Statistical Evaluation of Diagnostic Criteria for Bacterial Vaginosis", Am. J. Obstet. & Gynaecol., 162(1): 155–160 (1990).
10. Hillier, S., Krohn, M. A., Watts, D. H., Wolner-Hanssen, P., Eschenbach, D., "Microbiological Efficacy of Intravaginal Clindamycin Cream for the Treatment of Bacterial Vaginosis", Obstet. & Gynaecol., 76(3): 407–413 (1990).
11. Eschenbach, D. A., Hillier, S., Critchlow, C., Stevens, C., DeRouen, T., Holmes, K. K., "Diagnosis and Clinical Manifestations of Bacterial Vaginosis", Am. J. Obstet. & Gynaecol., 158(4): 819–828 (1988).

SUMMARY OF THE INVENTION

It is accordingly an object of the present invention to provide a very rapid method for the detection of polyamines. Another object of the invention is to provide a very rapid method for the detection of bacterial vaginosis. Yet a further object of the invention is to provide a kit for use in such methods. Other objects of the invention will be apparent from the description which follows. The term "very rapid" in the present context means within thirty minutes at the most.

Accordingly, the present invention provides a method for the detection of at least one polyamine associated with bacterial infection, which comprises contacting a sample suspected of containing polyamine-associated bacteria in aqueous medium at alkaline pH with indigo carmine and a water-miscible solvent for the at least one polyamine and the indigo carmine, and observing whether a blue color develops in five minutes indicating the presence of polyamine.

In accordance with a particular embodiment of the invention, there is provided a method for the detection of polyamines associated with a bacterial infection, which comprises at least steps (a), (b) and (c) of the following steps (a), (b), (c), (d) and (e), namely:
  (a) contacting a sample suspected of containing polyamine-associated bacteria with a liquid which comprises a mixture of sodium chloride and water;
  (b) mixing the thus-contacted liquid with a mixture of indigo carmine, sodium carbonate (preferably anhydrous) and dimethyl sulfoxide;
  (c) observing whether a blue color develops in five minutes indicating the presence of polyamines;
  (d) in the case that a blue color develops in step (c), visually comparing its intensity with a predetermined scale for estimating the presence and concentration of polyamines (a green coloration is considered to be clinically insignificant, a brown coloration indicates excessive amounts of polyamines and the sample must be diluted and the test repeated);
  (e) spectrophotometrically measuring the relative proportions of blue and green colorations in the test solution, in order to quantify the amount of polyamines present.

The present invention moreover provides in another embodiment, a test kit for use in a method for the detection of bacterial vaginosis associated with the presence of polyamines, which comprises the following separate components in a container:
  (1) a finely-ground admixture of indigo carmine and sodium carbonate;
  (2) a sodium chloride solution;
  (3) dimethyl sulfoxide; and as optional additional components, at least one of the following components (4), (5) and (6), namely:
  (4) a color scale for enabling the presence and concentration of polyamines to be estimated by comparing with said scale the intensity of the blue color which may be obtained by contacting a test specimen suspected of containing such polyamines with components (1), (2) and (3);

(5) a sterile swab for collecting said test specimen; and (6) a test vessel adapted for mixing components (1), (2) and (3), and said test specimen.

Illustratively, components (1), (2) and (3) of the kit of the invention may be: (1) a finely-ground admixture of 150 mg. of a 1:1000 (weight ratio) mixture of indigo carmine and sodium carbonate; (2) a solution of 0.9 g. NaCl in 100 ml. water and (3) 0.35 ml dimethyl sulfoxide.

DETAILED DESCRIPTION OF THE INVENTION

Figure 1:
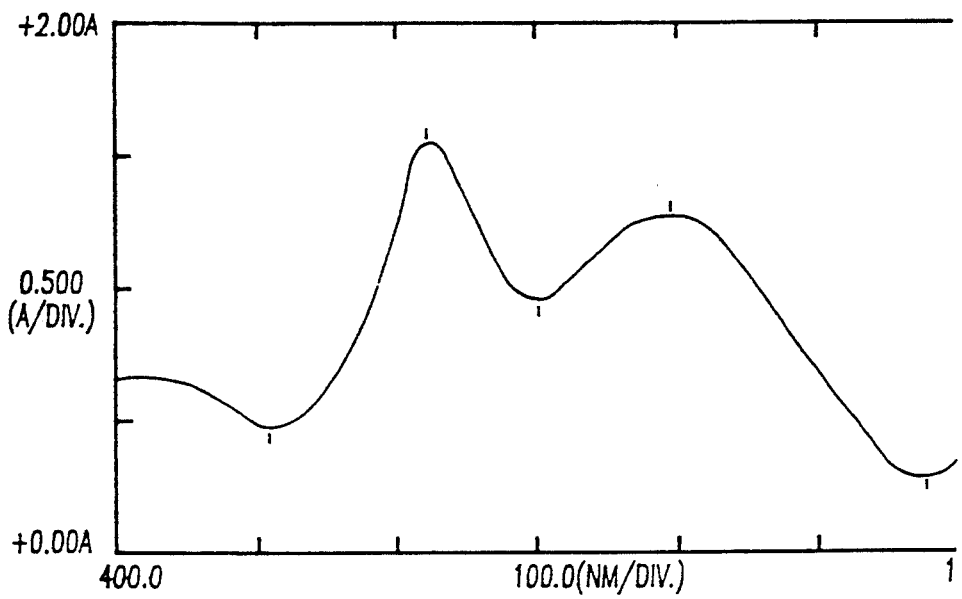
FIG. 1 illustrates a typical spectral curve obtained on spectrophotometric examination of a test sample in accordance with the invention.

The basis of the test in accordance with the invention is the formation of a blue color when one or more bacteria-associated polyamines are present and a green color when one or more bacteria-derived polyamines are absent. It is presently contemplated that at least the amines putrescine, cadaverine, spermine and spermidine can be detected by the method of the invention. The invention is especially useful for determining when an anaerobic vaginal infection associated with bacterial vaginosis is present in a test specimen taken from a patient.

For comparison purposes, the method of the invention was applied to separate test samples containing DL-ornithine; ammonium hydroxide; clinically normal and laboratory negative swabs of the vaginal cavity; and swabs from patients with positive yeast infections only. In all these cases, the method of the invention gave negative results. On the other hand, swabs taken from patients with a clinical and laboratory diagnosis of bacterial vaginosis, gave consistently positive results when tested by the method according to the present invention.

Dry solid indigo carmine and sodium carbonate (either alone or admixed together) were unchanged after several months in a sealed container, and reacted normally in the test, indicating that the shelf-life of these ingredients (including the admixture thereof) is at least one year.

EXAMPLE

A swab containing the test specimen is placed in an extraction fluid consisting of 0.9 g. NaCl in 100 ml. of water, and allowed to stand for five minutes. The swab is removed and 0.65 ml. of the extract is added to a cuvette containing a mixture of 0.35 ml. dimethyl sulfoxide with 150 mg. of an admixture of indigo carmine and sodium carbonate in a 1:1000 weight ratio. To ensure uniformity, separate samples of the solid indigo carmine/sodium carbonate admixture were previously passed through a coffee grinder for thirty seconds to form a fine powder, prior to use in the test. The mixture was shaken vigorously, and after five minutes the nature and intensity of the color was estimated using a calibrated color chart, or in addition the cuvette contents were subjected to quantitative spectrophotometric analysis. Negative swabs exhibited a green color, with an absorbance maximum of approximately 778 nanometers. Putrescine, cadaverine and positive swabs exhibit a blue color with an absorbance maximum at approximately 617 nanometers. For quantitative analysis, a working curve is obtained by plotting the concentration of polyamine(s) against the ratio of blue to green, i.e. ABS at 617 nm/ABS at 778 nm. A typical spectral curve, and a working curve, are shown as examples only in FIGS. 1 and 2, respectively. For convenience, the Table (below) lists the concentrations of putrescine and cadaverine obtained from the working curve. It should be appreciated that individuals operating the method of the invention will construct their own working curves.

TABLE

Relation of absorbance ratio to polyamine concentration.

| Absorbance ratio 617/778 nm | Polyamine concentration* mg/ml |
| --- | --- |
| 0.80 | 0.01 |
| 0.85 | 0.04 |
| 0.90 | 0.08 |
| 0.95 | 0.13 |
| 1.00 | 0.18 |
| 1.05 | 0.23 |
| 1.10 | 0.28 |
| 1.15 | 0.32 |
| 1.20 | 0.37 |
| 1.25 | 0.42 |
| 1.30 | 0.47 |
| 1.35 | 0.52 |
| 1.40 | 0.56 |
| 1.45 | 0.61 |
| 1.50 | 0.66 |
| 1.55 | 0.71 |
| 1.60 | 0.76 |
| 1.65 | 0.80 |
| 1.70 | 0.85 |

*Concentrations above 0.3 mg/ml are considered indicative of clinical bacterial vaginosis In FIG. 1, wavelength in nanometers (NM., X-axis) marked out as 100 nanometers/division, is plotted against absorbance of light (Y-axis) marked out as 0.5 units/division.

Figure 2:
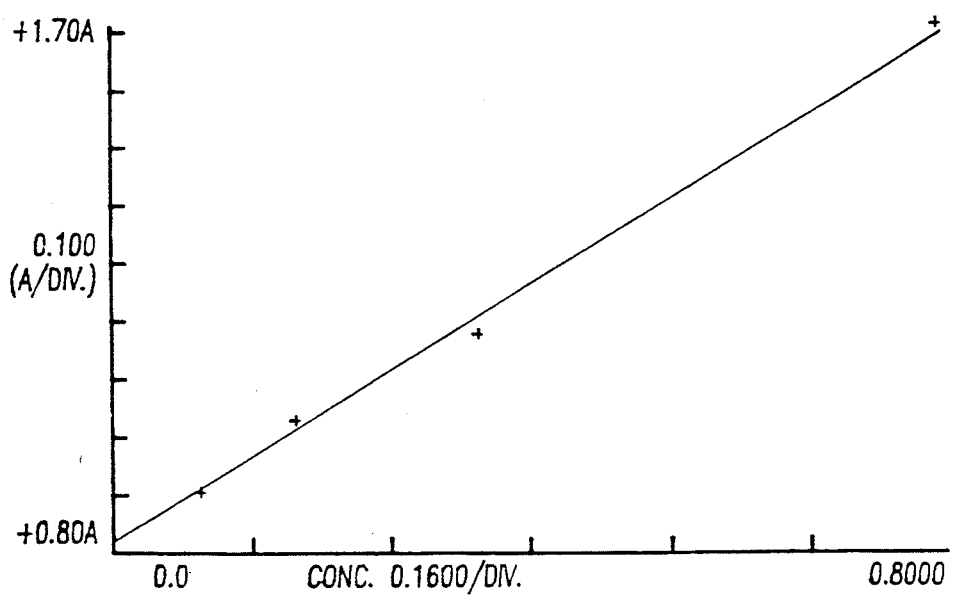
FIG. 2 shows a typical working curve relating the concentration of the polyamines putrescine and cadaverine in equal proportions by weight, to the ratios of optical absorbance at 617 nm relative to that at 778 nm.

In FIG. 2, concentration in mg/ml of putrescine + cadaverine (CONC=C, X-axis), marked out as 0.16 mg/ml per division, is plotted against the ratio of optical absorbance at 617 nm to that at 778 nm (A=ABS, Y-axis), marked out as 0.1 units/division. The equation (K)(ABS)+B is that of the line of best fit that connects the experimental data points, where K is the slope of the line of best fit, B is a constant, equal to the value of ABS when C=0, and C and ABS have the meanings already noted.

The results of clinical sampling of vaginal swabs for polyamines conducted on 104 females were as follows: sensitivity 75%; specificity 96%; positive predictive value 60%; negative predictive value 48%; efficiency 94%; prevalence 7.6%.

While the present invention has been particularly described in accordance with certain embodiments thereof, it will be apparent to skilled persons that many variations and modifications can be made. Illustratively, where certain embodiments of the invention use sodium chloride, it is believed that this functions to control the osmolarity and ionic strength of the extraction fluid close to that found in the human body; persons skilled in the art will be aware that there are other ways to achieve such control, e.g. by using other substances such as (e.g.) KCl, LiCl and urea, and the use of such other substances is considered to be within the scope of, and/or the chemical equivalents of, the use of NaCl in the methods and the kit of the invention. Accordingly, the invention is not to be construed as limited to such particularly described embodiments, rather its concept, spirit and scope can be appreciated by reference to the claims which follow.

We claim:

1. A method for detecting the presence of a polyamine in a sample in which a blue color forms when the polyamine is present and a green color forms when the polyamine is absent, comprising the step of:

contacting an aqueous sample containing a polyamine with a mixture of dimethyl sulfoxide and indigo carmine at an alkaline pH, wherein said blue color forms within five minutes indicating the presence of the polyamine.

2. The method of claim 1, further comprising comparing the intensity of said blue color formed with a predetermined scale for determining the presence or concentration of polyamines in a sample.

3. The method of claim 1, further comprising spectrophotometrically measuring the absorbance of said blue color and said green color and comparing the relative proportion of said blue color and said green color to a working curve obtained by plotting the concentration of said polyamine against relative proportions of said blue color and said green color.

4. The method of claim 1, wherein said polyamine is selected from the group consisting of putrescine, cadaverine, spermidine and spermidine.

5. The method of claim 4, wherein said polyamine is selected from the group consisting of putrescine and cadaverine.

6. The method of claim 1, wherein said aqueous sample is contacted with sodium carbonate to obtain said alkaline pH.

7. The method of claim 6, wherein said sodium carbonate is anhydrous.

8. The method of claim 1, wherein said aqueous sample contains sodium chloride, potassium chloride, lithium chloride or urea.

9. The method of claim 8, wherein said aqueous sample contains sodium chloride.

10. The method of claim 6, wherein the ratio of indigo carmine and sodium carbonate is 1:1000.

11. The method of claim 3, wherein the absorbance of said blue color is measured at 617 nm and the absorbance of said green color is measured at 778 nm.

12. The method of claim 1, wherein said sample is a vaginal sample from a patient suspected of exhibiting bacterial vaginosis.

13. A test kit for use in a method for the detection of a polyamine associated with bacterial vaginosis, which comprises the following separate components in a container:

(1) a finely ground admixture of indigo carmine and sodium carbonate;
(2) an aqueous solution of sodium chloride, potassium chloride, lithium chloride or urea; and
(3) dimethyl sulfoxide, in amounts sufficient to produce a blue colored solution in the presence of a polyamine.

14. The kit of claim 13, wherein said sodium carbonate is anhydrous.

15. The kit of claim 13, further comprising at least one member selected from the group consisting of (4) a color scale for enabling the presence or concentration of polyamines to be estimated by comparing the blue color formed in the presence of a polyamine with said scale, (5) a sterile swab, and (6) a test vessel adapted for mixing components (1), (2) and (3) in said sample.

16. The kit of claim 13, wherein said aqueous solution is a sodium chloride solution.

* * * * *